United States Patent
Fishman et al.

(10) Patent No.: US 9,387,220 B2
(45) Date of Patent: *Jul. 12, 2016

(54) METHOD FOR INDUCING HEPATOCYTE PROLIFERATION AND USES THEREOF

(71) Applicant: CAN-FITE BIOPHARMA LTD., Petach Tikva (IL)

(72) Inventors: Pnina Fishman, Herzliya (IL); Shira Cohen, Herzliya (IL)

(73) Assignee: CAN-FITE BIOPHARMA LTD., Petach Tikva (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/464,970

(22) Filed: Aug. 21, 2014

(65) Prior Publication Data

US 2014/0364388 A1 Dec. 11, 2014

Related U.S. Application Data

(63) Continuation of application No. 12/682,994, filed as application No. PCT/IL2008/001361 on Oct. 22, 2008, now Pat. No. 8,846,635.

(60) Provisional application No. 60/960,797, filed on Oct. 15, 2007.

(51) Int. Cl.
*A61K 31/7076* (2006.01)
*A61K 31/52* (2006.01)
*A61K 31/522* (2006.01)

(52) U.S. Cl.
CPC ............. *A61K 31/7076* (2013.01); *A61K 31/52* (2013.01); *A61K 31/522* (2013.01)

(58) Field of Classification Search
None
See application file for complete search history.

(56) References Cited

U.S. PATENT DOCUMENTS

| | | | |
|---|---|---|---|
| 5,443,836 A | 8/1995 | Downey et al. | |
| 5,573,772 A | 11/1996 | Downey et al. | |
| 5,688,774 A | 11/1997 | Jacobson et al. | |
| 5,773,423 A | 6/1998 | Jacobson et al. | |
| 6,048,865 A | 4/2000 | Baraldi | |
| 2004/0106572 A1 | 6/2004 | Fishman et al. | |
| 2005/0101560 A1 | 5/2005 | Warrington et al. | |
| 2006/0194756 A1* | 8/2006 | Borea et al. ............... | 514/45 |
| 2010/0222369 A1 | 9/2010 | Fishman et al. | |

FOREIGN PATENT DOCUMENTS

| | | |
|---|---|---|
| WO | 95/02604 A1 | 1/1995 |
| WO | 97/27173 A2 | 7/1997 |
| WO | 99/06053 A1 | 2/1999 |
| WO | 99/20284 A1 | 4/1999 |
| WO | 2004/045627 A1 | 3/2004 |
| WO | 2006/031505 A1 | 3/2006 |
| WO | 2007/071379 A1 | 6/2007 |

OTHER PUBLICATIONS

Chen et al., "Activation of Adenosine A3 Receptors Reduces Ischemic Brain Injury in Rodents" Journal of Neuroscience Research, 84(8):1848-1855 (2006).
Shirasugi et al., "Up-Regulation of Oxygen-Derived Free Radicals by Interleukin-1 in Hepatic Ischenlia/Reperfusion Injuryl" Transplantation, 64(10):1398-1403 (1997).
Teoh et al., "Hepatic Ischemic Preconditioning in Mice is Associated with Activation of NF-KB, p38 Kinase, and Cell Cycle Entry" Hepatology, 36(1):94-102 (2002).
Van Troostenburg et al., "Tolerability, Pharmacokinetics and Concentration-Dependent Hemodynamic Effects of Oral CF1 01, and A3 Adenosine Receptor Agonist, in Healthy Young Men" International Journal of Clinical Pharmacology and Therapeutics, 42(10):534-542 (2004).
Xu et al., "18-MECA and Cardioprotection" Cardiovascular Drug Reviews, 24(3-4):227-238 (2006).
Bar Yehuda et al., "Agonists to the A3 adenosine receptor induce G-CSF production via NF-KB activation: A new class of myeloprotective agents," Experimental Hematology, 30:1390-1398 (2002).
Fishman et al., "Adenosine and Other Low Molecular Weight Factors Released by Muscle Cells Inhibit Tumor Cell Growth," Cancer Research, 58:3181-3187 (1998).
Fishman et al., "Adenosine Acts as a Chemoprotective Agent by Stimulating G-CSF Production: A Role for A1 and A3 Adenosine Receptors," Journal of Cellular Physiology, 183:393-398 (2000).
Fishman et al., "The A3 Adenosine Receptor as a New Target for Cancer Therapy and Chemoprotection," Experimental Cell Research, 269:230-236.
Ge et al., "CI-IB-MECA [2-Chloro-N'-(3-iodobenzyl)adenosine-5'-N-methylcarboxamide] Reduces Ischemia/Reperfusion Injury in Mice by Activating the A3 Adenosine Receptor," The Journal of Pharmacology and Experimental Therapeutics, 319(3):1200-1210.
Lee et al. "A3 adenosine receptor activation decreases mortality and renal and hepatic injury in murine septic peritonitis," Am. J. of Physiol. Regul. Camp. Physiol., 291:R959-R969 (2006).
Kim et al., "Selective Ligands for Rat A3 Adenosine Receptors: Structure—Activity Relationships of 1,3-Dialkylxanthine 7-Riboside Derivatives," J. Med. Chem., 37:4020-4030 (1994).
Lim et al., "Design, Synthesis and Binding Affinity of 3'-Fiuoro Analogues of GI-IB-MEGA as Adenosine A3 Receptor Ligands," Bioorganic & Medicinal Chemistry Letters, 13:817-820 (2003).
Ohana, "Inhibition of primary colon carcinoma growth and liver metastasis by the A3 adenosine receptor agonist CF101 ," British Journal of Cancer, 89:1552-1558 (2003).

(Continued)

*Primary Examiner* — Layla Berry
(74) *Attorney, Agent, or Firm* — Browdy and Neimark, PLLC (57) ABSTRACT

The present application provides methods and compositions for inducing hepatocyte proliferation and liver regeneration, the latter being mainly dependent on hepatocyte proliferation even if all the other cell types divide to reconstitute the organ specific-lobular-architecture. The methods and compositions provided herein make use of an $A_3AR$ agonist. A preferred $A_3AR$ agonist disclosed herein is Cl-IB-MECA.

19 Claims, 4 Drawing Sheets

(56) References Cited

OTHER PUBLICATIONS

Guinzberg, "Inosine released after hypoxia activates hepatic glucose liberation through A3 adenosine receptors," Am. J. Physiol, Endocrinol, Metab., 290:E940-E951 (2006).

International Search Report mailed Jan. 30, 2009 in corresponding Application No. PCT/IL2008/001361.

Alcohol Alert, National Institute on Alcohol Abuse and Alcoholism, No. 64, Jan. 2005.

Bernuau et al. Gastroenterology, 90(2):268-73, abstract only (1986).

Wheeler et al., The New England Journal of Medicine, 340(3), 207-214 (1999).

"Definition of derivative", retrieved from Merriam-Webster online dictionary <<http://www.merriamwebster.com/dictionary/derivative>> on Apr. 6, 2011, 2 pages.

Wnuk, abstract of Med. Sci.Monit., 7(4), 729-736 (2001) Retrieved from online <http://www.ncbi.nlm.nih.gov/pubmed/11433202> on Oct. 25, 2011, 1 page.

\* cited by examiner

METHOD FOR INDUCING HEPATOCYTE PROLIFERATION AND USES THEREOF

FIELD OF THE INVENTION

This invention relates to the field of therapeutics and in particular to methods for inducing hepatocyte differentiation and liver regeneration.

PRIOR ART

The following is a list of art which is considered to be pertinent for describing the state of the art in the field of the invention. Acknowledgement of these references herein will at times be made by indicating their number within brackets from the list below.

1. Henrion J. Ischemia/reperfusion injury of the liver: pathophysioloic hypotheses and potential relevance to human hypoxic hepatitis. Acta Gastroenterol Belg. 63:336-347.
2. Shirasugi N, Wakabayashi G, Shimazu M. Up-regulation of oxygen-derived free radicals by interleukin-1 in hepatic ischemial/reperfusion injury. Transplantation 64:1398-403.
3. Xu Z, Jang Y, Mueller R A, Norfleet E A: IB-MECA and cardioprotection. Cardiovasc. Drug Rev. 24(3-4):227-238.
4. Chen G J, Harvey B K, Shen H, Chou J, Victor A, Wang Y: Activation of adenosine A3 receptors reduces ischemic brain injury in rodents. J. Neurosci. Res. 84(8):1848-1855.
5. Fishman P, Bar-Yehuda S, Farbstein T, Barer F, Ohana G: Adenosine acts as a chemoprotective agent by stimulating G-CSF production: a role for A1 and A3 adenosine receptors. J. Cell. Physiol. 183(3):393-398.
6. Fishman P, Bar-Yehuda S, Barer F, Madi L, Multani A F, Pathak S: The A3 adenosine receptor as a new target for cancer therapy and chemoprotection. Exp. Cell. Res. 269 (2): 230-236.
7. Bar-Yehuda S, Madi L, Barak D et al.: Agonists to the A3 adenosine receptor induce G-CSF production via NF-kappaB activation: a new class of myeloprotective agents. Exp. Hematol. 30(12):1390-1398.
8. Fishman P, Bar-Yehuda S, and Wagman L. (1998). Adenosine and other low molecular weight factors released by muscle cells inhibit tumor cell growth: Possible explanation for the rarity of metastases in muscle. Cancer Res. 58:3181-3187.
9. Fishman P, Bar-Yehuda S, Farbstein T, Barer F, and Ohana G. Adenosine acts as a chemoprotective agent by stimulating G-CSF production: A role for A1& A3 adenosine receptors. J. Cell. Physiol. 183:393-398.
10. Fishman P, Bar-Yehuda S, Barer F, Madi L, Multani Asha S, Pathak S. The A3 adenosine receptor as a new target for cancer therapy and chemoprotection. Exp Cell Res. 269: 230-236.
11. Teoh N, dela Pena A, Farrell G. Hepatic ischemia preconditioning in mice is associated with activation of $NF_{\kappa}B$. p38 kinase and cell cycle entry. Hepatology 36:94-102.

BACKGROUND OF THE INVENTION

The liver is the only vital organ, aside from the brain, for which there is no pharmacological, mechanical, or extra corporeal means of support for a failing organ, such as are found for the lungs, kidney and heart. The liver is also unique in that it is the only mammalian organ that can regenerate its biologically functional parenchymal mass following resection or injury, instead of healing with biologically nonfunctional scar tissue.

Liver resections have become safer in the past 10 years, owing to improvements in preoperative diagnosis, surgical techniques and postoperative care. Postoperative mortality correlates directly with preoperative liver function and resected liver volume. Function of the remnant liver rapidly recovers in patients with normal liver parenchyma as hepatocytes proliferate to restore the loss of volume. However, in the presence of parenchymal liver disease, as in patients with liver cirrhosis, severe liver steatosis or colorectal liver metastasis, debilitated by neoadjuvant chemotherapy before liver resection, hepatocellular proliferation is impaired, exposing patients to liver dysfunction and associated complications, culminating in posthepatectomy liver failure, which has a high mortality (60-90%).

Several pathways have been identified in the regenerating liver including a cytokine pathway that is largely responsible for the entry of hepatocytes into the cell cycle (transition from G0 to G1), a process that is known as priming, and a growth factor pathway that is responsible for cell-cycle progression (G1 phase to the S phase).

In addition, ischemia-reperfusion injury of the liver is another known, clinically significant manifestation of surgical procedures, such as liver transplantation and partial hepatic resection (1). There are two distinct phases of liver injury after ischemia-reperfusion injury. The initial phase (<2 h after reperfusion) is characterized by oxidant stress, where production and release of reactive oxygen species (ROS) appears to directly result in hepatocelluar injury. The late phase (6-48 h after reperfusion) is an inflammatory disorder mediated by recruited neutrophils. Interrelationships between products of activated Kupffer cells and neutrophils, such as tumor necrosis factor (TNF-α), interleukin (IL)-1, nitric oxide (NO) and leukotrienes, have been implicated in the pathogenesis of hepatic ischemia-reperfusion injury (2). The biological effects of TNF-α extend from inducing cell death to promoting cell regeneration.

Indeed, recent studies have shown that ischemic preconditioning may be associated with entry of hepatocytes into the cell cycle within 2 h of subsequent ischemia-reperfusion in a murine model of partial hepatic IR injury (11).

Adenosine, through its binding to selective G-protein-associated membrane receptors, designated as $A_1$, $A_{2A}$, $A_{2B}$ and $A_3$, accumulates extracellularly following ischemia, and is known to confer cytoprotection. In particular, the $A_3AR$ has been found to be involved in mediating cardio-neuro- and chemo-protection (3-7).

The $A_3$ adenosine receptor, a $G_i$ protein-associated cell surface receptor, has been proposed as a target to combat cancer and inflammation. The receptor is highly expressed in various tumor cell types while low expression was shown in adjacent normal tissues. In vivo studies have shown that $A_3AR$ agonists inhibit the development of colon, prostate and pancreatic carcinomas as well as melanoma and hepatoma.

$A_3AR$ agonists were also been shown to act as anti-inflammatory agents by ameliorating the inflammatory process in different experimental autoimmune models such as rheumatoid arthritis, Multiple sclerosis and Crohn's disease.

Moreover, $A_3AR$ agonists have been shown to possess a differential effect on tumor and normal cell growth. While activation of the $A_3AR$ inhibits the growth of various tumor cell lines, it stimulates the proliferation of normal cells such as bone marrow cells (8-10).

At present, there is no pharmacological intervention proven to either attenuate liver cell injury or to augment tissue regeneration of the liver after acute or chronic injury of this vital organ.

SUMMARY OF THE INVENTION

The present invention is based on the following findings obtained from experiments conducted in rats with Cl-IB-MECA, a specific and selective $A_3AR$ agonists:
- treatment with Cl-IB-MECA induced proliferation of hepatocytes after partial hepatectomy;
- treatment with Cl-IB-MECA reduced serum levels of the liver enzymes alanine aminotransferase (ALT) and aspartate aminotransferase (AST) after partial hepatectomy;
- treatment with Cl-IB-MECA increased the number of hepatocytes undergoing mitosis upon partial hepatectomy;
- treatment with Cl-IB-MECA increased the number of proliferation cell nuclear antigen (PCNA) positive cells (the expression correlating with degree of cell proliferation);
- treatment with Cl-IB-MECA increased liver weight.

Based on the above findings it has been concluded that $A_3AR$ agonists may be utilized for inducing hepatocytes' proliferation and liver regeneration.

Thus, in accordance with a first aspect, there is provided a method of stimulating hepatocytes' proliferation, comprising contacting hepatocytes with an $A_3AR$ agonist in an amount effective to stimulate hepatocytes' proliferation.

Further provided by the present disclosure is an $A_3AR$ agonist for use in a method for stimulating hepatocytes' proliferation.

In another embodiment, there is provided by the present disclosure an $A_3AR$ agonist for use in a method for treating a patient having liver damage, e.g. caused by a disease, e.g. cirrhosis, caused by a surgical treatment, e.g. due to hepatectomy and others.

The present disclosure also provides the use of an $A_3AR$ agonist for the preparation of a medicament for treating a liver damage in a patient.

Further, there is provided by the present disclosure a pharmaceutical composition for stimulating hepatocyte proliferation, comprising an $A_3AR$ agonist in an amount effective to stimulate hepatocytes' proliferation. Also provided by the present disclosure is a pharmaceutical composition for treating a liver damage, comprising an $A_3AR$ agonist in an amount effective to stimulate hepatocytes' proliferation.

In one embodiment, the $A_3AR$ agonist is 2-chloro-$N^6$-(3-iodobenzyl)-adenosine-5'-N-methyl-uronamide (Cl-IB-MECA), and in another embodiment, the $A_3AR$ agonist is $N^6$— (3-iodobenzyl)-adenosine-5'-N-methyl-uronamide (IB-MECA). However, these currently preferred $A_3AR$ agonists are by no means exclusive and other such $A_3AR$ agonists may also be used, as detailed further below.

In the context of the present disclosure, a variety of conditions in which the liver or liver cells are damaged following liver injury, hepatectomy, disease-induced or infection-induced liver damage may be treated by the use of an $A_3AR$ agonist.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF THE INVENTION

The invention is described in the following detailed description with reference to methods for the stimulation of hepatocyte proliferation and liver regeneration. It should be noted that in addition to said methods, also encompassed within the present invention is an $A_3AR$ agonist for use in a method for stimulating hepatocyte proliferation and liver regeneration; the use of an $A_3AR$ agonist for the preparation of a pharmaceutical composition for administration to a subject requiring stimulation of hepatocyte proliferation and liver regeneration; as well as a pharmaceutical composition for the stimulation of hepatocyte proliferation and liver regeneration, that comprises an effective amount of an $A_3AR$ agonist and a pharmaceutically acceptable carrier.

As used in the specification and claims, the forms "a", "an" and "the" include singular as well as plural references unless the context clearly dictates otherwise. For example, the term "an $A_3AR$ agonist" includes one or more agonists.

Further, as used herein, the term "comprising" is intended to mean that the methods or composition includes the recited elements, but not excluding others. Similarly, "consisting essentially of" is used to define methods and compositions that include the recited elements but exclude other elements that may have an essential significance on the stimulation of hepatocyte proliferation and liver regeneration. For example, a composition consisting essentially of an $A_3AR$ agonist will not include or include only insignificant amounts (amounts that will have an insignificant effect on the anti-inflammatory effect of the composition) of other active ingredients that have an hepatocyte proliferation and liver regeneration activity. Also, a composition consisting essentially of the active agents as defined herein would not exclude trace contaminants from the isolation and purification method, pharmaceutically acceptable carriers, excipients, preservatives, and the like. "Consisting of" shall mean excluding more than trace elements of other elements. Embodiments defined by each of these transition terms are within the scope of this invention.

Further, all numerical values, e.g., concentration or dose or ranges thereof, are approximations which are varied (+) or (−) by up to 20%, at times by up to 10% of from the stated values. It is to be understood, even if not always explicitly stated that all numerical designations should be read as if preceded by the term "about". It also is to be understood, although not always explicitly stated, that the reagents described herein are merely exemplary and that equivalents of such are known in the art.

As detailed in the following exemplary embodiment, the invention is based on the finding that $A_3AR$ agonists may be used to enhance liver regeneration.

Thus, $A_3AR$ agonists may be used in in vitro and in vivo methods of stimulating hepatocytes and promoting hepatocyte proliferation. In accordance with the methods disclosed herein, hepatocytes may be contacted with an amount of an $A_3AR$ agonist effective in inducing proliferation of the hepatocytes.

Such methods and uses include, by one embodiment, the addition of $A_3AR$ agonists to hepatocytes in vitro. Accordingly, there are disclosed methods and uses in culturing hepatocytes in vitro, e.g. for subsequent transplantation, for generating artificial liver tissue ex vivo, etc. Such methods and uses involve the provision of a biologically effective amount of an $A_3AR$ agonist to an in vitro or ex vivo biological sample that contains a population of hepatocytes.

Preferred methods, $A_3AR$ agonist, uses and pharmaceutical compositions in the context of the present disclosure are those in which the $A_3AR$ agonists are intended for induction of proliferation of hepatocytes in vivo, within the framework of a therapeutic treatment intended for inducing proliferation of hepatocytes to counter liver damages of the kind noted above and further below. Thus provides herein are methods, $A_3AR$ agonist, and uses of inducing liver growth, stimulating hepatic regeneration and, generally, treating subjects having various forms of liver damage and disease.

Within the framework of the present disclosure, the term "liver damage" is used to denote any type of hepatic trauma (injury), including chronic and acute trauma as well as pathological change present in liver cell or tissue. The clinical conditions of liver damage may include, without being limited thereto, degeneration of live cells, vasculitis of liver, spotty necrosis or focal necrosis present in liver, inflammatory cell infiltration or fibroblast proliferation in liver and portal area, or hepatomegaly, and hepatocirrhosis, hepatoma resulted from severe liver damage, and the like. The damage may be a result of a disease (i.e. disease induced) and/or toxicity hepatotoxic chemical substance-induced liver damage. It is known that some drugs can cause liver damage, and result in hepatic cytolysis and necrosis.

Within the framework of the present disclosure, the $A_3AR$ agonist is administered to a subject in amounts effective to promote hepatocyte proliferation, induce liver growth, stimulate hepatic regeneration and/or to generally treat or prevent liver damage, diseases and/or disorders in the animal or human patient. The terms "effective amounts" or "amount effective to", as used in the present specification refers to amounts effective to promote hepatocyte proliferation, induce liver growth, stimulate hepatic regeneration and/or treat or prevent liver damage when administered to an animal or human patient. The effective amount is preferably an amount yielding a concentration of the $A_3AR$ agonist in which it selectively activates the $A_3AR$ without activating any other adenosine receptor. For example, in the case of IB-MECA and Cl-IB-MECA such a preferred amount is an amount that will yield a concentration of less than about 200, 150, 125 or even less than about 100 nM in the case of IB-MECA and less than about 400, 300, 250, or even less than about 200 nM in the case of Cl-IB-MECA. The resulting concentration in an in vitro embodiment where induction of proliferation of hepatocytes is carried out in can be simply calculated or determined analytically. In the case of an in vivo administration to achieve proliferation of hepatocytes in vivo, e.g. within the framework of treating a liver injury, the effective amount may be determined through pharmacokinetic (PK) studies by measuring blood or plasma concentrations of the $A_3AR$ agonists at defined time intervals (by blood withdrawal at such times) following administration of the $A_3AR$ agonists. In PK studies the maximal concentration of the $A_3AR$ agonist in the blood or plasma should preferably be a concentration which is below that in which another adenosine receptor will be activated.

Induction of hepatocyte proliferation in the context of the present disclosure denotes the promotion or stimulation of hepatocyte division, and at times, the inhibition of hepatocyte death.

The $A_3AR$ agonists is preferably formulated for systemic administration, including oral, transdermal, intravenous, intraperitoneal, subcutaneous or intramuscular administration. More localized delivery to the liver is also contemplated, including all forms of intra-hepatic administration.

A wide range of diseases, disorders and conditions associated with liver damage may be treated by the $A_3AR$ agonists as disclosed herein. These include liver damage associated with exposure to alcohol, hepatotoxic drugs and combinations thereof. Exemplary damaging agents are anticonvulsants, phenyloin, carbamazepine and phenobarbital, and recreations drugs, such as that know as "Ecstasy" (3,4-methylenedioxymethamphetamine).

Side effects resulting from other therapies may also be treated in accordance with the present disclosure, including the liver damage associated with exposure to anti-tuberculosis agents and chemotherapeutic agents. the analgetic acetaminophen (i.e., Panadol, the chemical name of which is 4-(N-acetylamino)phenol), when administered in a large dose, is a kind of liver-damaging substance that can induce necrosis of human liver. For example, long-term administration of antibiotic, such as rifampicin, pyrazinamide, and isoniazide, and long-term administration of estrogen and the like in the period of menopause, also can cause severe hepatocyte necrosis, leading to liver damage, such as acute or chronic hepatitis, jaundice, and hepatic fibrosis and the like.

Liver damage associated with a reduction in viable liver tissue may also be treated, such as occurs after resecting a carcinoma.

Liver damage resulting from or associated with infectious agents may also be counteracted using the present invention. This includes liver damage associated with bacterial, parasitic, fungal and viral infections. For example, liver damage results from Aspergillus fungal infections, Schistosoma parasitic infections and a variety of viral infections, such as adenovirus, retrovirus, adeno-associated virus (AAV), hepatitis virus A, hepatitis virus B, hepatitis virus C, hepatitis virus E, herpes simplex virus (HSV), Epstein-Barr virus (EBV) and paramyxovirus infections, all of which may be treated hereby.

In the context of the present disclosure, $A_3AR$ agonists may also be utilized in the treatment or even prevention of liver damage associated with excess acetaminophen (paracetamol) ingestion. This may occur over a prolonged time period, leading to chronic liver damage; or during a short or immediate time period, leading to acute liver damage. The latter embodiments include deliberate and accidental overdoses, including in both adults and children.

Various $A_3AR$ agonists are known in the art. However, the invention is not limited to known $A_3AR$ agonists. Generally, the $A_3AR$ agonist is any compound that is capable of specifically binding to the adenosine $A_3$ receptor ("$A_3AR$"), thereby fully or partially activating said receptor to yield a therapeutic effect (in this particular case, an inductive effect on hepatocyte proliferation).

The $A_3AR$ agonist is thus a compound that exerts its prime effect through the binding and activation of the $A_3AR$. In accordance with one embodiment, this would mean that at the doses it is being administered it essentially binds to and activates only the $A_3R$. In a preferred embodiment, the $A_3AR$ agonist has a binding affinity ($K_i$) to the human $A_3AR$ of less than 1000 nM, desirably less than 500 nM, advantageously less 200 nM and even less than 100 nM, typically less than 50 nM, preferably less than 20 nM, more preferably less than 10 nM and ideally less than 5 nM. The lower the $K_i$, the lower the dose of the $A_3AR$ agonist (that may be used) that will be effective in activating the $A_3R$ and thus achieving a therapeutic effect.

By way of example, the $IC_{50}$ and $K_i$ of IB-MECA and Cl-IB-MECA, both specific $A_3AR$ agonists are shown in the following Tables 1 and 2:

TABLE 1

Binding Affinities of IB-MECA to the 4 adenosine receptors

| Receptor | $IC_{50}$ (nM) | $K_i$ (nM) |
|---|---|---|
| $A_1$ | >1,000 | Not determined |
| $A_{2A}$ | 685 | 560 |
| $A_{2B}$ | 47,600 | 42,300 |
| $A_3$ | 0.68 | 0.47 |

TABLE 2

Binding Affinities of Cl-IB-MECA to the 4 adenosine receptors

| Receptor | $IC_{50}$ (nM) | $K_i$ (nM) |
|---|---|---|
| $A_1$ | 5,390 | 3,140 |
| $A_{2A}$ | 2,090 | 1,170 |
| $A_{2B}$ | No activity | No activity |
| $A_3$ | 0.717 | 0.661 |

As these tables clearly show, both IB-MECA and Cl-IB-MECA are highly selective agonists to the $A_3AR$.

It should be noted that some $A_3AR$ agonists can also interact with and activate other receptors with lower affinities (namely a higher $K_i$). A compound will be considered an $A_3AR$ agonists in the context of the present disclosure (namely a compound that exerts its prime effect through the binding and activation $A_3AR$) if its affinity to the $A_3AR$ is at least 3 times (i.e. its $K_i$ to the $A_3AR$ is at least 3 times lower). Preferably the $A_3AR$ agonist used in the context of the present disclosure is an agent that specifically and selectively binds and activates the $A_3AR$. The $A_3AR$ agonist has thus an $IC_{50}$ or a $K_i$ that is preferably at least 10, 15, 20, 25, 50, 75, 100, 150, 250 or at time at least 500 times lower than the $IC_{50}$ or a $K_i$ to any other adenosine receptor.

The affinity of $A_3AR$ agonists to the human $A_3AR$ as well as its relative affinity to the other human adenosine receptors can be determined by a number of assays, such as a binding assay. Examples of binding assays include providing membranes or cells having the receptor and measuring the ability of the $A_3AR$ agonist to displace a bound radioactive agonist; utilizing cells that display the respective human adenosine receptor and measuring, in a functional assay, the ability of the $A_3AR$ agonist to activate or deactivate, as the case may be, downstream signaling events such as the effect on adenylate cyclase measured through increase or decrease of the cAMP level; etc. Clearly, if the administered level of an $A_3AR$ agonist is increased such that its blood level reaches a level approaching that of the $K_i$ of the other adenosine receptors, activation of these receptors may occur following such administration, in addition to activation of the $A_3R$. An $A_3AR$ agonist is thus preferably administered at a dose such that the blood level that will be attained will give rise to essentially only $A_3R$ activation.

The characteristic of some adenosine $A_3AR$ agonists and methods of their preparation are described in detail in, inter alia, U.S. Pat. No. 5,688,774; U.S. Pat. No. 5,773,423; U.S. Pat. No. 5,573,772; U.S. Pat. No. 5,443,836; U.S. Pat. No. 6,048,865; WO 95/02604; WO 99/20284; WO 99/06053; WO 97/27173 and WO/2006/031505 all of which are incorporated herein by reference.

According to one embodiment of the invention, the $A_3AR$ agonist is a purine derivative falling within the scope of the general formula (I):

(I)

wherein $R_1$ is $C_1$-$C_{10}$ alkyl, $C_1$-$C_{10}$ hydroxyalkyl, $C_1$-$C_{10}$ carboxyalkyl or $C_1$-$C_{10}$ cyanoalkyl or a group of the following general formula (II):

(II)

in which:
Y is oxygen, sulfur atom or $CH_2$;
$X_1$ is hydrogen, $C_1$-$C_{10}$ alkyl, $R^aR^bNC(=O)$— or $HOR^c$—, wherein $R^a$ and $R^b$ may be the same or different and are selected from hydrogen, $C_1$-$C_{10}$ alkyl, amino, $C_1$-$C_{10}$ haloalkyl, $C_1$-$C_{10}$ aminoalkyl, $C_1$-$C_{10}$ BOC-aminoalkyl, and $C_3$-$C_{10}$ cycloalkyl or are joined together to form a heterocyclic ring containing two to five carbon atoms, and $R^c$ is selected from $C_1$-$C_{10}$ alkyl, amino, $C_1$-$C_{10}$ haloalkyl, $C_1$-$C_{10}$ aminoalkyl, $C_1$-$C_{10}$ BOC-aminoalkyl, and $C_3$-$C_{10}$ cycloalkyl;
$X_2$ is hydrogen, hydroxyl, $C_1$-$C_{10}$ alkylamino, $C_1$-$C_{10}$ alkylamido or $C_1$-$C_{10}$ hydroxyalkyl;
$X_3$ and $X_4$ each independently are hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_3$ and $X_4$ are oxygen connected to >C=S to form a 5-membered ring, or $X_2$ and $X_3$ form the ring of formula (III):

(III)

where R' and R" are independently $C_1$-$C_{10}$ alkyl;
$R_2$ is selected from hydrogen, halo, $C_1$-$C_{10}$ alkylether, amino, hydrazido, $C_1$-$C_{10}$ alkylamino, $C_1$-$C_{10}$ alkoxy, $C_1$-$C_{10}$ thioalkoxy, pyridylthio, $C_2$-$C_{10}$ alkynyl; $C_2$-$C_{10}$ alkynyl, thio, and $C_1$-$C_{10}$ alkylthio; and $R_3$ is a —$NR_4R_5$ group with $R_4$ being hydrogen or a group selected from alkyl, substituted alkyl or aryl-NH—C(Z)—, with Z being O, S, or $NR^a$, and when $R_4$ is hydrogen, $R_5$ being selected from R- and S-1-phenylethyl, benzyl, phenylethyl or anilide groups, each said groups being unsubstituted or substituted in one or more positions with a substituent selected from $C_1$-$C_{10}$ alkyl, amino, halo, $C_1$-$C_{10}$ haloalkyl, nitro, hydroxyl, acetoamido, $C_1$-$C_{10}$ alkoxy, and sulfonic acid or a salt thereof; or $R_5$ is benzodioxanemethyl, fururyl, L-propylalanyl-aminobenzyl, β-alanylamino-benzyl, T-BOC-β-alanylaminobenzyl, phenylamino, carbamoyl, phenoxy or $C_1$-$C_{10}$ cycloalkyl; or $R_5$ is a group of the following formula (IV):

(IV)

or, when $R_4$ is alkyl, substituted alkyl, or aryl-NH—C(Z)—, then, $R_5$ is selected from the group consisting of substituted or unsubstituted heteroaryl-$NR^a$—C(Z)—, heteroaryl-C(Z)—, alkaryl-$NR^a$—C(Z)—, alkaryl-C(Z)—, aryl-NR—C(Z)— and aryl-C(Z)—;

or the $A_3AR$ agonist is a xanthine-7-riboside derivative of the following general formula (V):

(V)

wherein:
X is O or S;
$R_6$ is $R^aR^bNC(\!\!=\!\!O)$— or $HOR^c$—, wherein
$R^a$ and $R^b$ may be the same or different and are selected from hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl, or are joined together to form a heterocyclic ring containing two to five carbon atoms; and
$R^c$ is selected from $C_1$-$C_{10}$ alkyl, amino, $C_1$-$C_{10}$ haloalkyl, $C_1$-$C_{10}$ aminoalkyl, $C_1$-$C_{10}$ BOC-aminoalkyl and $C_3$-$C_{10}$ cycloalkyl;
$R_7$ and $R_8$ may be the same or different and are selected from $C_1$-$C_{10}$ alkyl, $C_1$-$C_{10}$ cycloalkyl, R- or S-1-phenylethyl, an unsubstituted benzyl or anilide group, and a phenylether of benzyl group substituted in one or more positions with a substituent selected from $C_1$-$C_{10}$ alkyl, amino, halo, $C_1$-$C_{10}$ haloalkyl, nitro, hydroxyl, acetamido, $C_1$-$C_{10}$ alkoxy, and sulfonic acid;
$R_9$ is selected from the group consisting of halo, benzyl, phenyl, $C_3$-$C_{10}$ cyclalkyl, and $C_1$-$C_{10}$ alkoxy;
or a suitable salt of the compound defined above.

In one embodiment, Y may form a fused bridge with either of the substituents $X_1$ or $X_2$. This embodiment is disclosed in WO 2006/031505, whose entire contents are incorporated by reference. In a further embodiment, such compounds may have the following general formula:

(VI)

wherein $X_1$, $R_2$ and $R_5$ are as defined above.

According to another embodiment, the A3AR agonist is a nucleoside derivative of the general formula (VII):

(VII)

wherein $X_1$, $R_2$ and $R_5$ are as defined above.

A non-limiting group of $A_3AR$ agonists are the $N^6$-benzyladenosine-5'-uronamide derivatives. Some preferred $N^6$-benzyladenosine-5'-uronamide derivatives are $N^6$-2-(4-aminophenyl)ethyladenosine (APNEA), $N^6$-(4-amino-3-iodobenzyl)adenosine-5'-(N-methyluronamide) (AB-MECA), 1-deoxy-1-{6-[({3-iodophenyl}methyl)amino]-9H-purine-9-yl}-N-methyl-β-D-ribofuranuronamide (IB-MECA) and 2-chloro-$N^6$-(3-iodobenzyl)adenosine-5'-N-methlyuronamide (Cl-IB-MECA).

According to another embodiment, the $A_3AR$ agonist is $N^6$-benzyl-adenosine-5'-alkyluronamide-$N^1$-oxide or $N^6$-benzyladenosine-5'-N-dialyl-uronamide-$N^1$ oxide.

It is appreciated that the effective amount of the $A_3AR$ agonist depends on a variety of factors including the affinity of the active agent to its corresponding receptor, its distribution profile within the body, a variety of pharmacological parameters such as half life in the body, on undesired side effects, if any, on factors such as weight, age, gender, treatment history, concomitant medications, and other parameters of the subject to be treated, etc. The effective amount is typically tested in clinical studies having the aim of finding the effective dose range, the maximal tolerated dose and the optimal dose. The manner of conducting such clinical studies is well known to a person versed in the art of clinical development.

An amount may also at times be determined based on amounts shown to be effective in animals. It is well known that an amount of X mg/Kg administered to rats can be converted to an equivalent amount in another species (notably humans) by the use of one of possible conversions methods well known in the art. Examples of conversion equations are as follows:

Conversion I:

| Species | Body Wt. (Kg) | Body Surf. Area (m$^2$) | Km Factor |
|---|---|---|---|
| Mouse | 0.2 | 0.0066 | 3.0 |
| Rat | 0.15 | 0.025 | 5.9 |
| Human Child | 20.0 | 0.80 | 25 |
| Adult | 70.0 | 1.60 | 37 |

Body Surface area dependent Dose conversion: Rat (150 g) to Man (70 Kg) is 1/7 the rat dose. This means that in the resent case 0.001-0.4 mg/Kg in rats equals to about 0.14-56 microgram/Kg in humans; assuming an average weight of 70 Kg, this would translate into an absolute dosage of about 0.01 to about 4 mg.

Conversion II:

The following conversion factors: Mouse=3, Rat=67. Multiply the conversion factor by the animal weight to go from mg/Kg to mg/m$^2$ for human dose equivalent.

| Species | Weight (Kg) | BSA (m$^2$) |
|---|---|---|
| Human | 70.00 | 1.710 |
| Mouse | 0.02 | 0.007 |
| Rat | 0.15 | 0.025 |
| Dog | 8.00 | 0.448 |

According to this equation the amounts equivalent to 0.001-0.4 mg/Kg in rats for humans are 0.16-64 μg/Kg; namely an absolute dose for a human weighing about 70 Kg of about 0.011 to about 4.4 mg, similar to the range indicated in Conversion I.

Conversion III:

Another alternative for conversion is by setting the dose to yield the same plasma level or AUC as that achieved following administration to an animal.

An effective amount of an active agent may also be determined based on human PK studies. For example, human studies as described in US patent application, publication No. 20050101560 and by Fishman et al. [Fishman P. et al., Tolerability, pharmacokinetics, and concentration-dependent hemodynamic effects of oral CF101, an A3 adenosine receptor agonist, in healthy young men *Int J Clin Pharmacol Ther.* 42:534-542, 2004, (CF101 being a clinical grade, manufactured under cGMP guidelines, IB-MECA)] showed that the level of orally-administered IB-MECA decays in the human plasma from its peak concentration with a half life of about 8-10 hours, as compared to a half life of only 1.5 hours in mice, in case of multiple daily administration, correction in the dosages for accumulative effects needs to be made at times (a subsequent dose is administered before the level of a previous one was decayed and thus, there is a build-up of plasma level over that which occurs in a single dose. On the basis of said human trials twice daily administration appears to be a preferred administration regiment. However this does not rule out other administration regiments. Human studies conducted with Cl-IB-MECA showed that the level of orally-administered Cl-IB-MECA decays in the human plasma with a half life of about 12-14 hours fro its peak concentration. On the basis of this human data, the administration regiment in human subjects may preferably be once or twice daily although other regiments cannot be excluded.

In the context of the present invention, the pharmaceutical composition typically comprises a combination of an A3AR agonist with a pharmaceutically acceptable carrier as well as other additives. The carrier may at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. Examples of carriers, stabilizers and adjuvants, are described, for example, in E. W. Martin, REMINGTON'S PHARMACEUTICAL SCIENCES, MacK Pub Co (June, 1990).

The invention has been described in an illustrative manner, and it is to be understood that the terminology which has been used, is intended to be in the nature of words of description rather than of limitation. Obviously, many modifications and variations of the present invention are possible in light of the above teaching. It is therefore, to be understood that within the scope of the appended claims, the invention may be practiced otherwise than as specifically described hereinafter.

DETAILED DESCRIPTION OF NON-LIMITING EXEMPLARY EMBODIMENTS

Material & Methods

Animals

Male Wistar rats (275-300 g) were fasted 12 h before the procedure. The rats were anaesthetized with Ketamin (45 mg/kg) and Xylazine (5 mg/kg). Laparatomy was performed via a sub costal, bilateral incision. The main portal pedicle to the total liver was clamped for a period of 10 minutes, during which, a 70% hepatectomy was performed. After 10 minutes of ischemia (in the course of the hepatectomy), blood flow was restored by de-clamping.

Materials

The A$_3$AR agonist Cl-IB-MECA was synthesized for Can-Fite BioPharma by Albany Molecular Research Inc, Albany, N.Y., USA. Cl-IB-MECA was administered at a concentration of 100 μg/kg starting at the end of the ischemia, thrice daily for 48 h. Control rats did not receive Cl-IB-MECA Methods Rats underwent laparatomy and the main portal pedicle to the total liver was clamped for a period of 10 minutes, during which a 70% hepatectomy was performed. After 10 minutes of ischemia blood flow was restored by de-clamping. Cl-IB-MECA (100 μg/Kg) was administered orally, TID, starting at the perfusion.

Results

Hepatocyte Proliferation

Figure 1:
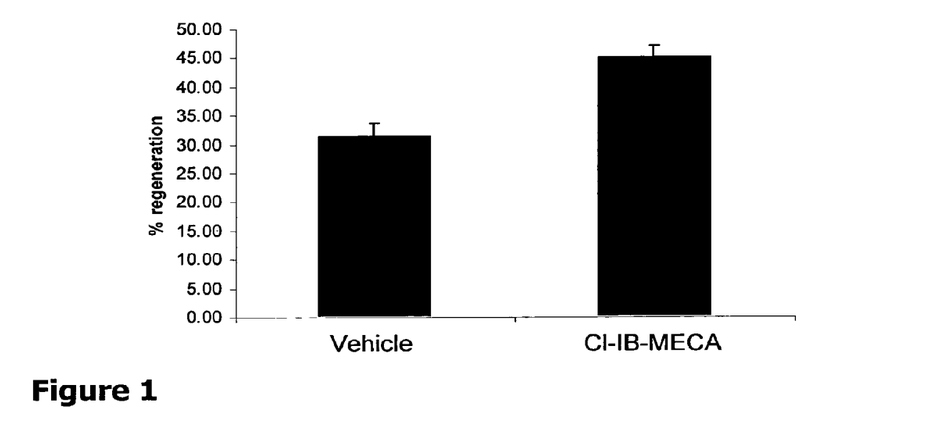
FIG. 1 is a bar graph showing the effect of Cl-IB-MECA (Treated) on the proliferation of hepatocytes in the liver of a rat undergoing liver regeneration after partial hepatectomy.

With reference to FIG. 1, it may be seen CL-IB-MECA upregulated hepatocyte proliferation of regenerated liver after partial hepatectomy, demonstrating a 45.1% level of regeneration in the treated group, as compared to 30% in the control group.

Serum Levels of the Liver Enzymes ALT and AST

Figure 2A:
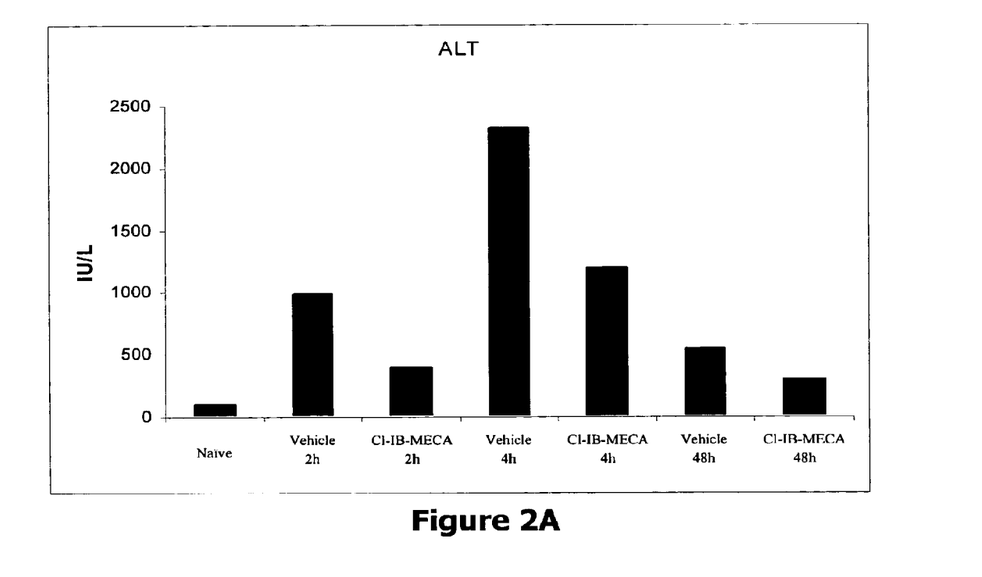
FIGS. 2A and 2B are bar graphs showing the serum levels of the liver enzymes alanine aminotransferase (ALT) (FIG. 2A) and aspartate aminotransferase (AST) (FIG. 2B) in rats treated with Cl-IB-MECA as compared to control rats, 2, 4 and 48 hours after partial hepatectomy.
Figure 2B:
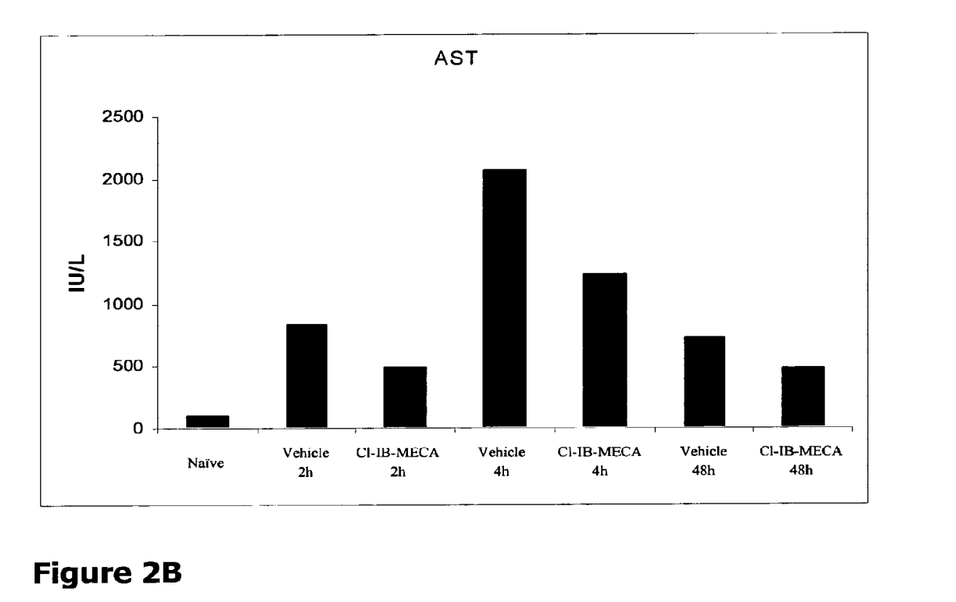

An increase in ALT and AST serum levels indicates liver damage. As can be seen from FIGS. 2A and 2B, the ALT and AST levels were significantly decreased in the CL-IB-MECA treated group as compared to the control group at each of the three time points measured (2, 4 and 48 hours).

Figure 3:
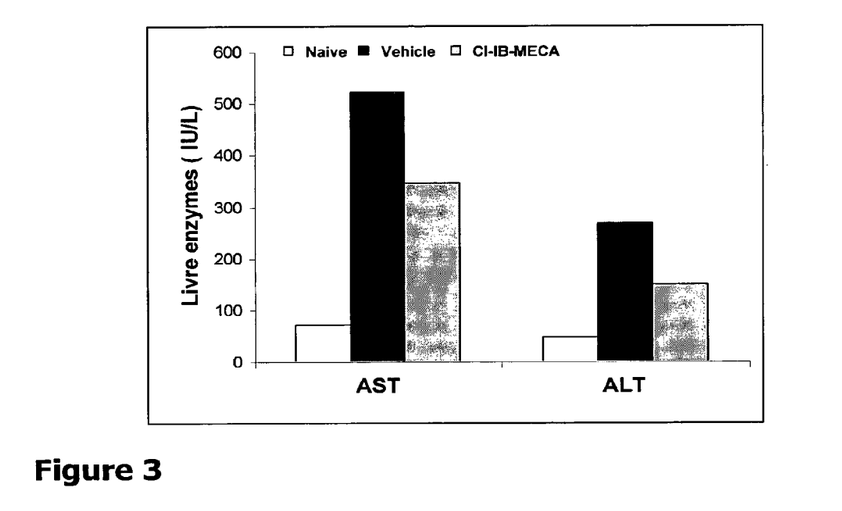
FIG. 3 is a bar graph showing serum levels of the liver enzymes AST and ALT in rats which underwent partial hepatectomy and treated Cl-IB-MECA as compared to untreated rats (naïve) or rats treated with vehicle (vehicle).

In a further assay, the effect of Cl-IB-MECA was compared to rats treated with the vehicle only, or to rats that received no treatment and the results are presented in FIG. 3. As shown, treatment with Cl-IB-MECA led to the reduction in serum levels of liver enzymes thereby demonstrating that Cl-IB-MECA treatment may protect liver against the damage induced by the ischemia/reperfusion procedure.

Mitotic Index

Figure 4:
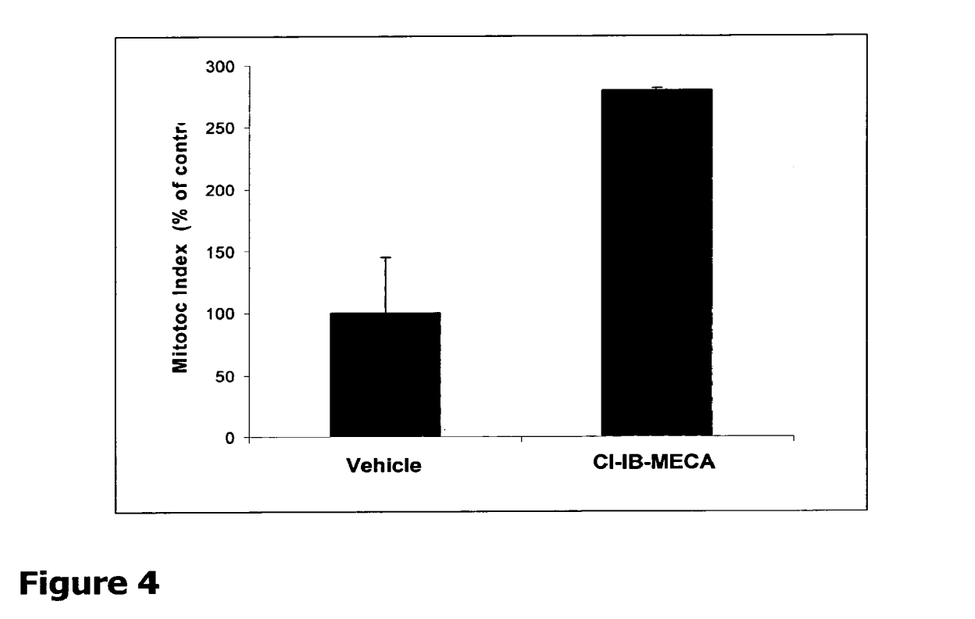
FIG. 4 is a bar graph showing mitotic index of hepatocytes in rats which underwent partial hepatectomy and treated with Cl-IB-MECA, as compared to rats treated with vehicle (vehicle).

Forty eight hours after partial hepatectomy the livers were collected, fixed with 10% buffered formalin and embedded in paraffin and 5 μm thick sections were subjected to Hematoxyline&Eosin staining. High power fields (HPF, 400-fold magnification) were screened and cells undergoing mitosis were counted for each field. FIG. 4 presents an average of 50 HPF counted. The results are presented as % of control. As shown, Cl-IB-MECA treatment significantly increased the mitotic index (P=0.035) in comparison to the vehicle-treated group.

Proliferating Cell Nuclear Antigen Expression

Figure 5A:
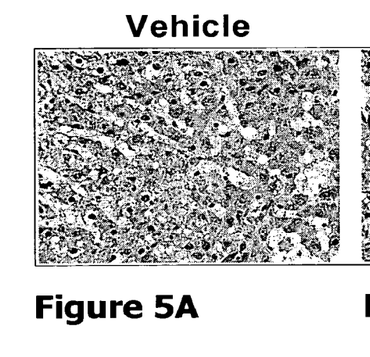
FIGS. 5A-5B are microscopic images following proliferating cell nuclear antigen (PCNA) staining of hepatocytes 48 hours after partial hepatectomy following treatment with vehicle only (FIG. 5A, vehicle) or with Cl-IB-MECA (FIG. 5B).
Figure 5B:
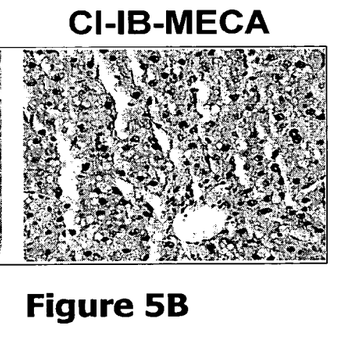

Proliferating cell nuclear antigen (PCNA) is a nuclear protein that is expressed in the late $G_1$ and throughout the S-phase of the cell cycle. The amount of PCNA expression correlates with the degree of cell proliferation. Forty eight hours after partial hepatectomy the livers were collected, fixed with 10% buffered formalin and embedded in paraffin and 5 μm thick sections were subjected to PCNA staining. The amount of PCNA following treatment with vehicle only or with Cl-IB-MECA is shown in FIGS. 5A and 5B, respectively. As shown, Cl-IB-MECA treatment significantly increased the number of PCNA positive hepatocytes (FIG. 5B).

Liver Regeneration

Figure 6:
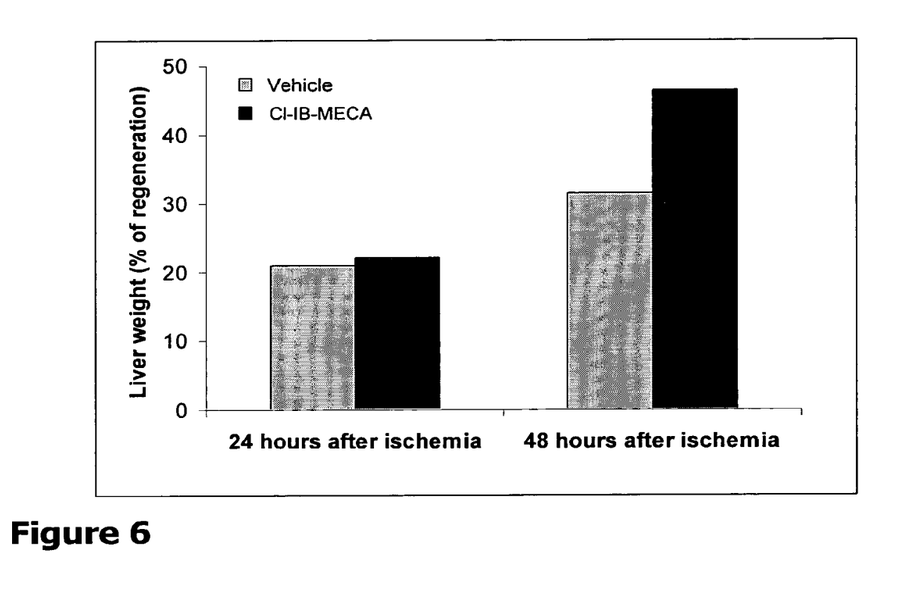
FIG. 6 is a bar graph showing liver weight (% of regeneration) 24 and 48 hours following partial hepatectomy in Cl-IB-MECA treated or rats treated with vehicle only (vehicle).

Livers were collected 24 and 48 hours after the partial hepatocytes and weight. The growth of residual liver lobes was assessed using the following equation:

$$\text{Hepatic regeneration rate}(\%) = \frac{C - (A - B)}{A \times 100}$$

where

A is the estimated total liver weight before hepatectomy (3.4% of a rat's total weight), B is the weight of liver resected during the hepatectomy, and C is the weight of the regenerated liver at the end of the study.

A shown, Cl-IB-MECA treatment led to an increase in liver weight, and in other words, accelerated the rate of liver regeneration.

Thus, it was concluded that the $A_3AR$ agonist Cl-IB-MECA is effective in regenerating the resected liver and preventing liver damage after hepatectomy.

The invention claimed is:

1. A method comprising providing to a subject known to have liver damage, only after the liver damage has occurred, a selective agonist of the $A_3$ adenosine receptor ($A_3AR$) in an amount effective to stimulate hepatocyte proliferation or liver regeneration in said subject, wherein said subject known to have liver damage is a subject having liver damage induced by a condition selected from the group consisting of hepatectomy, cirrhosis of the liver, hepatic malignancies, infectious agents, the side effects of gene therapy, and exposure to any one of anti-tuberculosis agents, chemotherapeutic agents, acetaminophen (APAP) overdoses, alcohol, and hepatotoxic drugs.

2. The method of claim 1, wherein the $A_3AR$ agonist is a purine derivative falling within the scope of the general formula (I):

wherein $R_1$ is $C_1$-$C_{10}$ alkyl, $C_1$-$C_{10}$ hydroxyalkyl, $C_1$-$C_{10}$ carboxyalkyl or $C_1$-$C_{10}$ cyanoalkyl or a group of the following general formula (II):

in which:

Y is oxygen, sulfur atom or $CH_2$;

$X_1$ is hydrogen, $C_1$-$C_{10}$ alkyl, $R^a R^b NC(=O)$— or $HOR^c$—, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, $C_1$-$C_{10}$ BOC-aminoalkyl, and $C_3$-$C_{10}$ cycloalkyl, or are joined together to form a heterocyclic ring containing two to five carbon atoms, and $R^c$ is selected from the group consisting of $C_1$-$C_{10}$ alkyl, amino, $C_1$-$C_{10}$ haloalkyl, $C_1$-$C_{10}$ aminoalkyl, $C_1$-$C_{10}$ BOC-aminoalkyl, and $C_3$-$C_{10}$ cycloalkyl;

$X_2$ is hydrogen, hydroxyl, $C_1$-$C_{10}$ alkylamino, $C_1$-$C_{10}$ alkylamido or $C_1$-$C_{10}$ hydroxyalkyl;

$X_3$ and $X_4$ each independently are hydrogen, hydroxyl, amino, amido, azido, halo, alkyl, alkoxy, carboxy, nitrilo, nitro, trifluoro, aryl, alkaryl, thio, thioester, thioether, —OCOPh, or —OC(=S)OPh, or both $X_3$ and $X_4$ are oxygen connected to >C=S to form a 5-membered ring, or $X_2$ and $X_3$ form the ring of formula (III):

where

R' and R" are independently $C_1$-$C_{10}$ alkyl;

$R_2$ is selected from the group consisting of hydrogen, halo, $C_1$-$C_{10}$ alkylether, amino, hydrazido, $C_1$-$C_{10}$ alkylamino, $C_1$-$C_{10}$ alkoxy, $C_1$-$C_{10}$ thioalkoxy, pyridylthio, $C_2$-$C_{10}$ alkenyl; $C_2$-$C_{10}$ alkynyl, thio, and $C_1$-$C_{10}$ alkylthio; and $R_3$ is a —$NR_4R_5$ group with $R_4$ being selected from the group consisting of hydrogen, alkyl, substituted alkyl and aryl-NH—C(Z)—, with Z being O, S, or $NR^a$ with $R^a$ having the above meaning, and when $R_4$ is hydrogen, $R_5$ is selected from the group consisting of R- and S-1-phenylethyl, benzyl, phenylethyl and anilide groups, each said groups being unsubstituted or substituted in one or more positions with a substituent selected from the group consisting of $C_1$-$C_{10}$ alkyl, amino, halo, $C_1$-$C_{10}$ haloalkyl, nitro, hydroxyl, acetoamido, $C_1$-$C_{10}$ alkoxy, and sulfonic acid or a salt thereof; or $R_5$ is benzodioxanemethyl, fururyl, L-propylalanylaminobenzyl, β-alanylaminobenzyl, T-BOC-β-alanylaminobenzyl, phenylamino, carbamoyl, phenoxy or $C_1$-$C_{10}$ cycloalkyl; or $R_5$ is a group of the following formula (IV):

(IV)

or, when $R_4$ is alkyl, substituted alkyl, or aryl-NH—C(Z)—, then, $R_5$ is selected from the group consisting of substituted or unsubstituted heteroaryl-$NR^a$—C(Z)—, heteroaryl-C(Z)—, alkaryl-$NR^a$—C(Z)—, alkaryl-C(Z)—, aryl-NR—C(Z)— and aryl-C(Z)—;

or the $A_3AR$ agonist is a xanthine-7-riboside derivative of the following general formula (V):

(V)

wherein:
X is O or S;
$R_6$ is $R^aR^bNC(=O)$— or $HOR^c$—, wherein
$R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl, or are joined together to form a heterocyclic ring containing two to five carbon atoms; and
$R^c$ is selected from the group consisting of $C_1$-$C_{10}$ alkyl, amino, $C_1$-$C_{10}$ haloalkyl, $C_1$-$C_{10}$ aminoalkyl, $C_1$-$C_{10}$ BOC-aminoalkyl and $C_3$-$C_{10}$ cycloalkyl;

$R_7$ and $R_8$ may be the same or different and are selected from the group consisting of $C_1$-$C_{10}$ alkyl, $C_1$-$C_{10}$ cycloalkyl, R- or S-1-phenylethyl, an unsubstituted benzyl or anilide group, and a phenylether of benzyl group substituted in one or more positions with a substituent selected from the group consisting of $C_1$-$C_{10}$ alkyl, amino, halo, $C_1$-$C_{10}$ haloalkyl, nitro, hydroxyl, acetamido, $C_1$-$C_{10}$ alkoxy, and sulfonic acid; and $R_9$ is selected from the group consisting of halo, benzyl, phenyl, $C_3$-$C_{10}$ cycloalkyl, and $C_1$-$C_{10}$ alkoxy;

or a suitable salt of the compound defined above.

3. The method of claim 2, wherein the $A_3AR$ agonist is $N^6$-benzyladenosine-5'-uronamide.

4. The method of claim 3, wherein the $A_3AR$ agonist is selected from the group consisting of $N^6$-2-(4-aminophenyl) ethyladenosine (APNEA), $N^6$-(4-amino-3-iodobenzyl), adenosine-5'-(N-methyluronamide), (ABMECA), 1-deoxy-1-{6-[({3-iodophenyl}methyl)amino]-9H-purine-9-yl}-N-methyl-β-D-ribofuranuronamide (IB-MECA), and 2-chloro-$N^6$-(3-iodobenzyl)adenosine-5'-N-methlyuronamide (Cl-IB-MECA).

5. The method of claim 4, wherein the $A_3AR$ agonist is IB-MECA or Cl-IB-MECA.

6. The method of claim 5, wherein the $A_3AR$ agonist is Cl-IB-MECA.

7. The method of claim 5, wherein said amount of selective $A_3AR$ agonist provided is an amount effective to stimulate hepatocyte proliferation in the liver of said subject.

8. A method according to claim 1, wherein said selective $A_3AR$ agonist comprises an adenosine backbone.

9. A method according to claim 1, wherein said selective $A_3AR$ agonist has an affinity to $A_3AR$ that is at least three times greater than to any other adenosine receptor.

10. The method of claim 1, wherein the liver damage is induced by hepatectomy.

11. The method of claim 1, wherein the liver damage is induced by cirrhosis of the liver.

12. The method of claim 1, wherein the liver damage is induced by a hepatic malignancy.

13. The method of claim 1, wherein the liver damage is induced by an infectious agent.

14. The method of claim 1, wherein the liver damage is induced by gene therapy.

15. The method of claim 1, wherein the liver damage is induced by exposure to an anti-tuberculosis agent.

16. The method of claim 1, wherein the liver damage is induced by exposure to a chemotherapeutic agent.

17. The method of claim 1, wherein the liver damage is induced by exposure to acetaminophen (APAP) overdoses.

18. The method of claim 1, wherein the liver damage is induced by exposure to alcohol.

19. The method of claim 1, wherein the liver damage is induced by exposure to a hepatotoxic drug.

* * * * *